(12) United States Patent
Park

(10) Patent No.: US 9,498,752 B2
(45) Date of Patent: Nov. 22, 2016

(54) DEVICES USING MEMBRANE MEDIATED FORWARD OSMOSIS

(71) Applicant: Fosmo Med, Inc., San Mateo, CA (US)

(72) Inventor: Benjamin B. Park, San Mateo, CA (US)

(73) Assignee: FOSMO MED, INC., San Mateo, CA (US)

( * ) Notice: Subject to any disclaimer, the term of this patent is extended or adjusted under 35 U.S.C. 154(b) by 605 days.

(21) Appl. No.: 13/938,063

(22) Filed: Jul. 9, 2013

(65) Prior Publication Data

US 2014/0008298 A1 Jan. 9, 2014

Related U.S. Application Data

(60) Provisional application No. 61/669,593, filed on Jul. 9, 2012, provisional application No. 61/714,920, filed on Oct. 17, 2012.

(51) Int. Cl.

| | |
|---|---|
| *B01D 61/00* | (2006.01) |
| *B01D 65/08* | (2006.01) |
| *A61J 1/20* | (2006.01) |
| *B01D 63/08* | (2006.01) |
| *B01D 67/00* | (2006.01) |
| *C02F 1/44* | (2006.01) |
| *A61M 5/14* | (2006.01) |
| *B01D 69/12* | (2006.01) |
| *C02F 103/02* | (2006.01) |

(52) U.S. Cl.
CPC ............ *B01D 61/002* (2013.01); *A61J 1/2093* (2013.01); *A61M 5/14* (2013.01); *B01D 63/087* (2013.01); *B01D 65/08* (2013.01); *B01D 67/0088* (2013.01); *B01D 69/12* (2013.01); *C02F 1/445* (2013.01); *B01D 2311/2626* (2013.01); *B01D 2313/20* (2013.01); *B01D 2325/12* (2013.01); *C02F 2103/026* (2013.01); *Y10T 29/49826* (2015.01)

(58) Field of Classification Search
CPC ............ B01D 61/002; B01D 67/0088; B01D 63/087; C02F 1/445; C02F 2103/026
See application file for complete search history.

(56) References Cited

U.S. PATENT DOCUMENTS

| | | |
|---|---|---|
| 4,810,388 A | 3/1989 | Trasen |
| 4,969,884 A | 11/1990 | Yum |

(Continued)

FOREIGN PATENT DOCUMENTS

| | | |
|---|---|---|
| CN | 1850645 A | 10/2006 |
| KR | 19960003544 A1 | 3/1996 |

(Continued)

OTHER PUBLICATIONS

International Search Report, PCT/US2013/049801, Oct. 15, 2013.

*Primary Examiner* — Bradley Osinski

(57) ABSTRACT

A forward osmosis device, method of manufacturing the forward osmosis device and method of using a solution produced using the forward osmosis device utilizes a forward osmosis membrane element positioned within a housing of the device between an input chamber and an output chamber to draw liquid from the input chamber to the output chamber via an osmotic process. The forward osmosis membrane element includes a layer of purifying additives on the forward osmosis membrane element to remove contaminants in the liquid as the liquid is drawn through the forward osmosis membrane element. In an embodiment, the forward osmosis device is a forward osmosis intravenous (IV) bag.

25 Claims, 11 Drawing Sheets

(56) References Cited

U.S. PATENT DOCUMENTS

| | | |
|---|---|---|
| 5,259,954 A | 11/1993 | Taylor |
| 5,725,777 A | 3/1998 | Taylor |
| 5,951,863 A | 9/1999 | Kruger et al. |
| 6,099,734 A * | 8/2000 | Boggs ............... B01D 63/087 210/263 |
| 6,110,498 A | 8/2000 | Rudnic et al. |
| 6,428,505 B1 | 8/2002 | Taylor |
| 6,471,688 B1 | 10/2002 | Harper et al. |
| 6,534,090 B2 | 3/2003 | Puthli et al. |
| 6,595,941 B1 | 7/2003 | Blatter |
| 6,849,184 B1 | 2/2005 | Lampi et al. |
| 7,250,619 B2 | 7/2007 | Taylor et al. |
| 7,560,029 B2 | 7/2009 | McGinnis |
| 8,216,473 B2 | 7/2012 | Wohlert |
| 2004/0004037 A1 * | 1/2004 | Herron ............... A61K 31/70 210/321.83 |
| 2004/0226444 A1 | 11/2004 | Leahey |
| 2011/0044824 A1 | 2/2011 | Kelada |
| 2011/0284456 A1 | 11/2011 | Brozell |
| 2012/0080377 A1 | 4/2012 | Jensen et al. |
| 2012/0080378 A1 | 4/2012 | Revanur et al. |
| 2012/0152841 A1 | 6/2012 | Vissing et al. |
| 2012/0228222 A1 | 9/2012 | McGinnis et al. |

FOREIGN PATENT DOCUMENTS

| | | |
|---|---|---|
| KR | 102003002514 A | 3/2003 |
| WO | 0051701 A2 | 9/2000 |
| WO | 2005077335 A1 | 8/2005 |

* cited by examiner

DEVICES USING MEMBRANE MEDIATED FORWARD OSMOSIS

CROSS REFERENCE TO RELATED APPLICATION

This application is entitled to the benefit of U.S. Provisional Patent Application Ser. No. 61/669,593, filed on Jul. 9, 2012, and U.S. Provisional Patent Application Ser. No. 61/714,920, filed on Oct. 17, 2012, which are incorporated herein by reference.

BACKGROUND OF THE INVENTION

There are many medical treatments that require sterile liquids. One type of such medical treatments is intravenous (IV) therapy, which involves the infusion of liquid substance directly into a vein. In many instances, an IV solution is delivered to a patient using an IV line from an IV bag containing the IV solution to the patient. The IV solution contained in the IV bag can vary depending on the medical needs of the patient. As an example, the IV solution in the IV bag may be a saline or glucose solution. The IV line from the IV bag can be used to deliver different types of medications or drugs.

A concern with conventional IV bags is that these IV bags are heavy and bulky, and thus, are expensive to transport over long distances. While conventional IV bags are inexpensive, e. g., a typical 0.9% saline solution IV bag is less than $3, the shipping cost for these IV bags can be very high, e.g., over $15 in many cases.

A concern with IV medications is that some drugs cannot be premixed into solutions due to rapid loss of potency and/or short shelf life. That is, some drugs must be mixed with sterile solution near the time of use, for example, less than 24 hours. Thus, there must be a supply of sterile solution at the site of use or a supply of sterile solution must be transported along with the drugs, which can be expensive depending on the distance to the site of use.

SUMMARY OF THE INVENTION

A forward osmosis device, method of manufacturing the forward osmosis device and method of using a solution produced using the forward osmosis device utilizes a forward osmosis membrane element positioned within a housing of the device between an input chamber and an output chamber to draw liquid from the input chamber to the output chamber via an osmotic process. The forward osmosis membrane element includes a layer of purifying additives on the forward osmosis membrane element to remove contaminants in the liquid as the liquid is drawn through the forward osmosis membrane element. In an embodiment, the forward osmosis device is a forward osmosis intravenous (IV) bag.

A forward osmosis device in accordance with an embodiment of the invention comprises a housing, draw solutes and a forward osmosis membrane element. The housing has an input chamber and an output chamber. The housing includes an inlet connected to the input chamber and an outlet connected to the output chamber. The draw solutes are contained in the output chamber of the housing. The forward osmosis membrane element is positioned within the housing between the input chamber and the output chamber. The forward osmosis membrane element is configured to draw liquid placed in the input chamber through the inlet into the output chamber containing the draw solutes via an osmotic process. The forward osmosis membrane element includes a layer of purifying additives on the forward osmosis membrane element to remove contaminants in the liquid as the liquid is drawn through the forward osmosis membrane element.

A method of manufacturing a forward osmosis device in accordance with an embodiment of the invention comprises providing a forward osmosis membrane element, providing housing components, providing draw solutes, applying purifying additives onto the forward osmosis membrane element, thereby forming a layer of purifying additives on the forward osmosis membrane element, and assembling the forward osmosis membrane element with the layer of purifying additives, the housing components, and the draw solutes to produce the forward osmosis device that includes a housing having an input chamber and an output chamber separated by the forward osmosis membrane, the output chamber containing the draw solutes, the housing including an inlet connected to the input chamber and an outlet connected to the output chamber so that liquid can be placed in the input chamber through the inlet to produce a solution in the output chamber and the solution in the chamber can be accessed through the outlet.

A method of using a solution produced using a forward osmosis device that includes a housing having an input chamber and an output chamber separated by a forward osmosis membrane element, the forward osmosis membrane element including a layer of purifying additives on the forward osmosis membrane element, in accordance with an embodiment of the invention comprising receiving liquid into the input chamber of a housing of the forward osmosis device, drawing the liquid from the input chamber of the housing to the output chamber of the housing through the forward osmosis membrane element via an osmotic process, including transmitting the liquid through the layer of purifying additives to remove contaminants in the liquid as the liquid is drawn through the forward osmosis membrane element, and forming the solution containing the draw solutes and the drawn liquid in the output chamber of the housing.

A forward osmosis intravenous (IV) bag in accordance with an embodiment of the invention comprises an IV bag housing, draw solutes and a forward osmosis membrane element. The IV bag housing has an input chamber and an output chamber. The IV bag housing includes an inlet connected to the input chamber and an exit port connected to the output chamber. The exit port is designed to be connected to an IV line. The draw solutes are contained in the output chamber of the IV bag housing. The forward osmosis membrane element is positioned within the IV bag housing between the input chamber and the output chamber. The forward osmosis membrane element is configured to draw water placed in the input chamber into the output chamber containing the draw solutes via an osmotic process to produce an IV solution in the output chamber of the IV bag housing. The output chamber is accessible via the exit port when the exit port is connected to the IV line to allow the IV solution to flow from the output chamber to a patient through the IV line.

A method of manufacturing a forward osmosis IV bag in accordance with an embodiment of the invention comprises providing a forward osmosis membrane element, providing IV bag housing components, providing draw solutes, and assembling the forward osmosis membrane element, the IV bag housing components, and the draw solutes to produce the forward osmosis IV bag that includes an IV bag housing having an input chamber and an output chamber separated by the forward osmosis membrane element. The output chamber containing the draw solutes. The IV bag housing includes an inlet configured to receive water into the input chamber that is drawn to the output chamber by the draw solutes through the forward osmosis membrane element to produce a IV solution. The IV bag housing further includes an exit port that is designed to be connected to an IV line.

A method of using an IV solution produced using a forward osmosis IV bag that includes an IV bag housing having an input chamber and an output chamber separated by a forward osmosis membrane element in accordance with an embodiment of the invention comprises receiving water into the input chamber of the IV bag housing of the forward osmosis IV bag, drawing the water from the input chamber of the IV bag housing to the output chamber of the IV bag housing through the forward osmosis membrane element via an osmotic process, forming the IV solution containing the draw solutes and the drawn liquid in the output chamber of the IV bag housing, and connecting an IV line to an exit port of the IV bag housing of the forward osmosis IV bag to allow the IV solution to flow from the output chamber of the IV bag housing to a patient through the IV line.

Other aspects and advantages of the present invention will become apparent from the following detailed description, taken in conjunction with the accompanying drawings, illustrated by way of example of the principles of the invention.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

Figure 1:
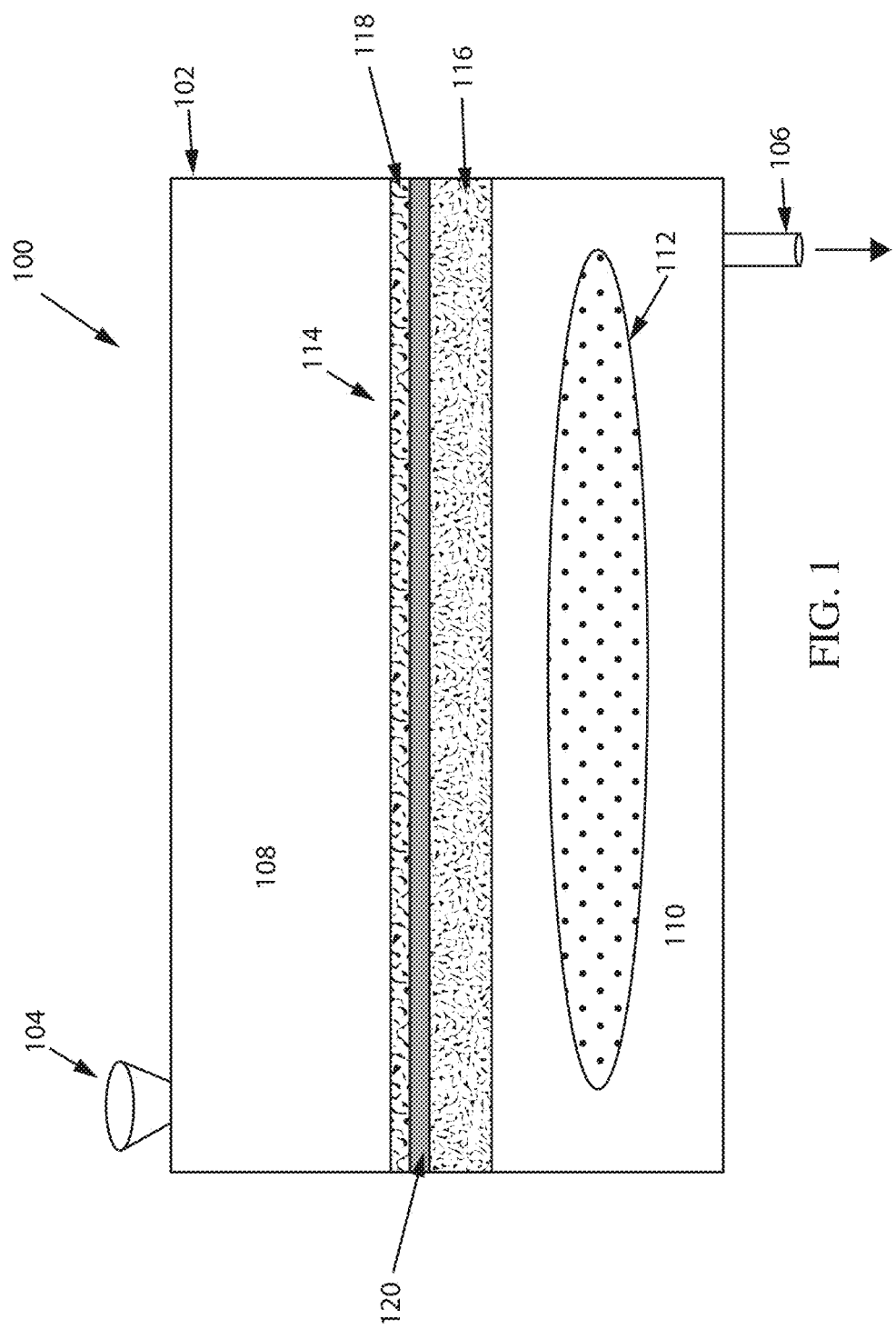
FIG. 1 is a diagram of a forward osmosis device in accordance with an embodiment of the invention.

Turning now to FIG. 1, a forward osmosis device 100 in accordance with an embodiment of the invention is shown. As described in detail below, the forward osmosis device uses forward osmosis to provide clean or sterile liquid, which can be used for various purposes, such as human consumption and medical applications. As an example, the forward osmosis device can be used as a water purification device to provide drinking water from any source of water, even wastewater. As another example, the forward osmosis device can be used as a medical device that produces a sterile solution from non-sterile liquid that can be used for intravenous administration, wound cleansing or drug reconstitution. However, the forward osmosis device can be used as any device that uses or provides clean or sterile solution.

As shown in FIG. 1, the forward osmosis device 100 includes a housing 102 with an inlet 104 and an outlet 106. The housing can be made of any material, which may be transparent or opaque. For example, the housing can be made of clear plastic. In some embodiments, the housing may be flexible so that the device can expand when filled with liquid. However, in other embodiments, the housing may be made of hard material so that the housing is fairly inflexible. In some embodiments, the housing is made from more than one component that are integrated to form the housing. For example, if the housing is a bag, the components of the housing may include each side of the bag. The inlet of the housing allows liquid to place in the forward osmosis device, while the outlet of the housing allows processed liquid to exit from the forward osmosis device. The inlet and the outlet of the housing may be simple openings that can be closed using caps or other types of sealing mechanisms. In some embodiments, the outlet may be closed until punctured or otherwise opened.

The housing 102 is configured to include an input chamber 108 and an output chamber 110. The input chamber is used to receive liquid, which may be contaminated with undesirable chemicals and/or materials, through the inlet 104. The output chamber is used to hold processed liquid, i.e., processed or filtered liquid. The output chamber contains draw solutes 112 to draw the input liquid from the input chamber to the output chamber via an osmotic process.

The draw solutes 112 contained in the output chamber 110 of the forward osmosis device 100 may be any suitable material for membrane mediated forward osmosis process. The draw solutes may include substances from a "salt" family, such as sodium chloride, potassium chlorides and magnesium chloride, or may include substances from a "sucrose" family, such as sugar and dextrose. These types of draw solutes may be used to produce a saline or sucrose solution. However, in other embodiments, the draw solutes may include other types of elements that are suitable for membrane mediated forward osmosis process to produce other types of solutions. The draw solutes may be in the form of a brine or in the form of solids.

The forward osmosis device 100 also includes a forward osmosis membrane element 114 that separates the input chamber 108 and the output chamber 110. The forward osmosis membrane element includes a forward osmosis membrane 116, which can be any forward osmosis membrane. As an example, the forward osmosis membrane 116 may be osmosis membrane manufactured by HTI, ZNano, Porifera or others. Forward osmosis membranes are well known, and thus, the forward osmosis membrane 116 is not described herein in detail. When the input chamber 108 of the housing 102 is filled with liquid, the forward osmosis membrane 116 draws the liquid from the input chamber to the output chamber 110 of the housing due to the brine or sludge containing the draw solutes 112 in the output chamber (the brine is formed in the output chamber if the draw solutes were originally in solid form by the liquid that seeps through the forward osmosis membrane from the input chamber).

The forward osmosis membrane 116 is configured so that most of contaminants in the input liquid are filtered as the liquid travels through the forward osmosis membrane. However, the resulting liquid may not be sufficiently free of contaminants, especially for medical purposes. For example, the resulting liquid may not meet US Food and Drug Administration guidelines for medical use. Thus, one or both major sides of the forward osmosis membrane are pretreated with purifying additives to create one or more layers 118 of purifying additives to further filter out contaminants before the liquid is drawn through the forward osmosis membrane (only one layer of purifying additives is shown in FIG. 1). That is, the major surface of the forward osmosis membrane facing the input chamber 108 and/or the major surface of the forward osmosis membrane facing the output chamber 110 are pretreated with purifying additives. In an embodiment, the pretreatment of one of the major surfaces of the forward osmosis membrane with the purifying additives involves mixing the purifying additives with base liquid and then applying the mixture to the surface of the forward osmosis membrane. The base liquid, which can be any liquid, is used to maintain flexibility and pliability of the applied forward osmosis membrane. The ratio of the base liquid versus the purifying additives is based on the type of purifying additives being used. The purifying additives can be any substance that removes or filters any contaminants found in any liquid, such as water. As an example, the purifying additives may be activated charcoal powder (e.g., coconut shell activated carbon powder) or Hydromethane Sulfinate for ammonia removal. In some embodiments, multiple types of purifying additives, either in solid or liquid form, can be added to the base liquid to produce the mixture. In an embodiment, the additive mixture is then applied to one or more major surfaces of the forward osmosis membrane by spraying the mixture onto the surfaces of the forward osmosis membrane.

In an embodiment, the forward osmosis membrane 116 is an asymmetric forward osmosis membrane and may include a porous non-active layer 120 facing the input chamber 108. In this embodiment, the outer surface of the porous non-active layer is pretreated with purifying additives before the asymmetric forward osmosis membrane 116 is used in the manufacturing of the forward osmosis device 100.

Figure 2:
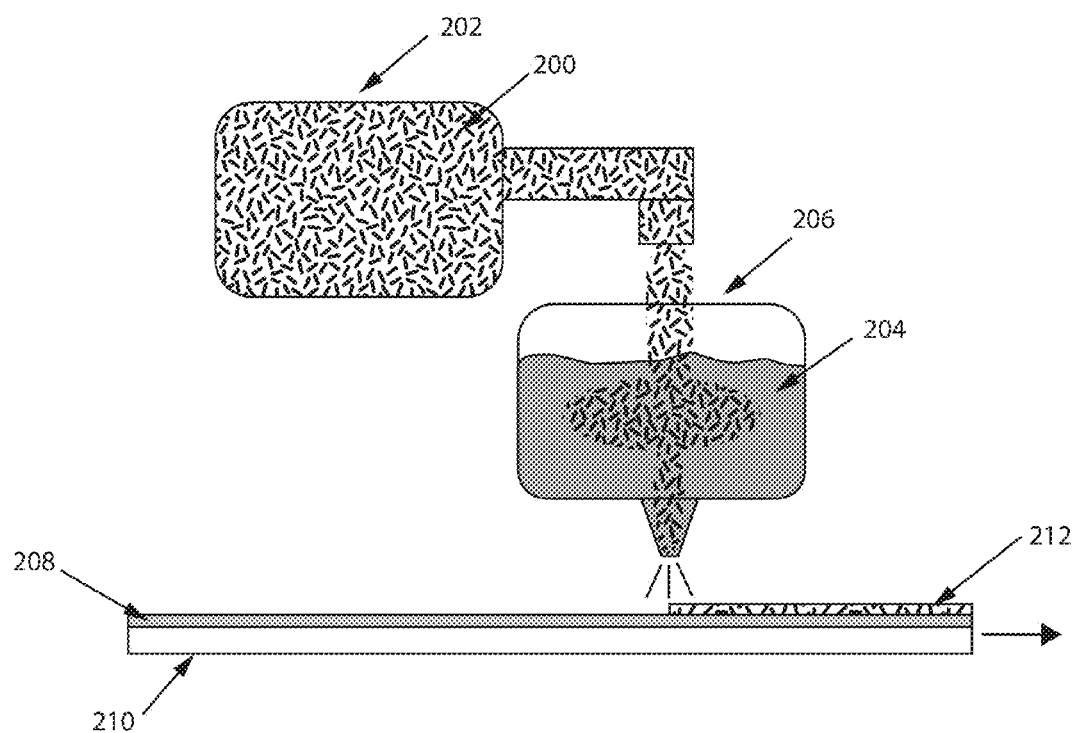
FIG. 2 is an illustration of a process of forming a layer of purifying additives on a asymmetrical forward osmosis membrane in accordance with an embodiment of the invention.

FIG. 2 illustrates the pretreatment process of a porous non-active layer of an asymmetric forward osmosis membrane in accordance with an embodiment of the invention. As shown in FIG. 2, one or more types of purifying additives 200 from a supply 202 of purifying additives are mixed with a base liquid 204 in a spraying device 206. Alternatively, the purifying additives may be premixed with the base liquid and placed in the spraying device. The mixture containing the purifying additives is then sprayed onto a non-active layer 208 of an asymmetric forward osmosis membrane 210 forming a layer 212 of purifying additives on the surface of the non-active layer of the asymmetric forward osmosis membrane. In the illustrated embodiment, the asymmetric forward osmosis membrane is displaced relative to the spraying device as the mixture is being sprayed onto the surface of the non-active layer. However, in other embodiments, the spraying device may be displaced relative to the asymmetric forward osmosis membrane as the mixture is being sprayed onto the surface of the non-active layer. After the asymmetric forward osmosis membrane has been treated with the additive mixture, the treated asymmetric forward osmosis membrane and other components of the forward osmosis device 100 are assembled to manufacture the forward osmosis device 100.

In another embodiment, the layer 118 of purifying additives of the forward osmosis membrane element 116 may be a porous substrate, which contains the purifying additives, that is attached or placed adjacent to an untreated forward osmosis membrane, i.e., a forward osmosis membrane that has not been treated with purifying additives. In this embodiment, the porous substrate is a component not found in a conventional forward osmosis membrane. The porous substrate may be treated in a similar manner as illustrated in FIG. 2 before or after the porous substrate is attached or placed adjacent to the untreated forward osmosis membrane.

Figure 3:
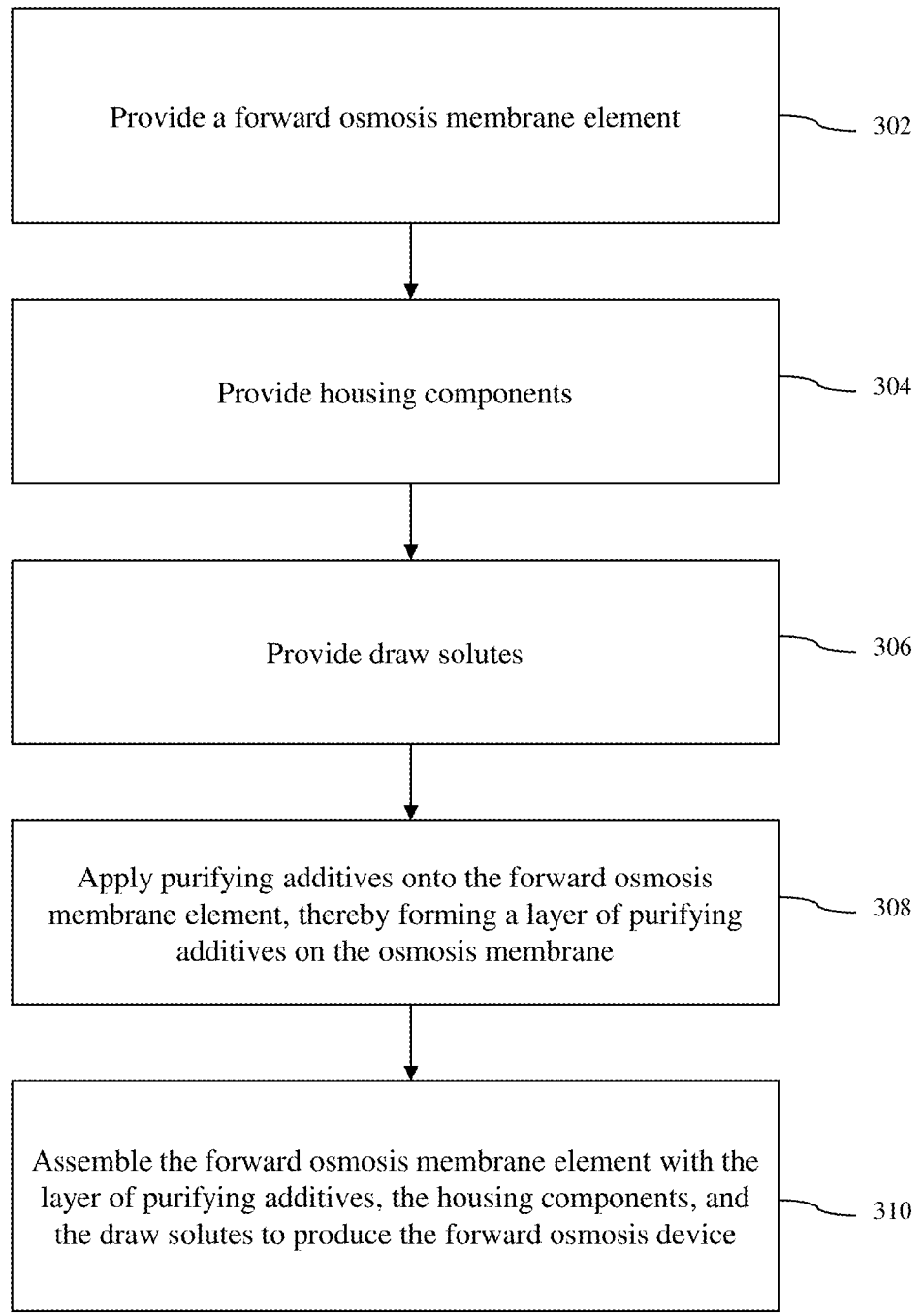
FIG. 3 is a process flow diagram of a method of manufacturing a forward osmosis device in accordance with an embodiment of the invention.

A method of manufacturing a forward osmosis device, such as the forward osmosis device of FIG. 1, in accordance with an embodiment of the invention is now described with reference to the process flow diagram of FIG. 3. At block 302, a forward osmosis membrane element is provided. At block 304, housing components are provided. At block 306, draw solutes are provided. At block 308, purifying additives are applied onto the forward osmosis membrane element, thereby forming a layer of purifying additives on the osmosis membrane. At block 310, the forward osmosis membrane element with the layer of purifying additives, the housing components, and the draw solutes are assembled to produce the forward osmosis device that includes a housing having an input chamber and an output chamber separated by the forward osmosis membrane. These components of the forward osmosis device are assembled so that the output chamber containing the draw solutes and the housing includes an inlet connected to the input chamber and an outlet connected to the output chamber so that liquid can be placed in the input chamber through the inlet to produce a solution in the output chamber and the solution in the chamber can be accessed through the outlet.

Figure 4:
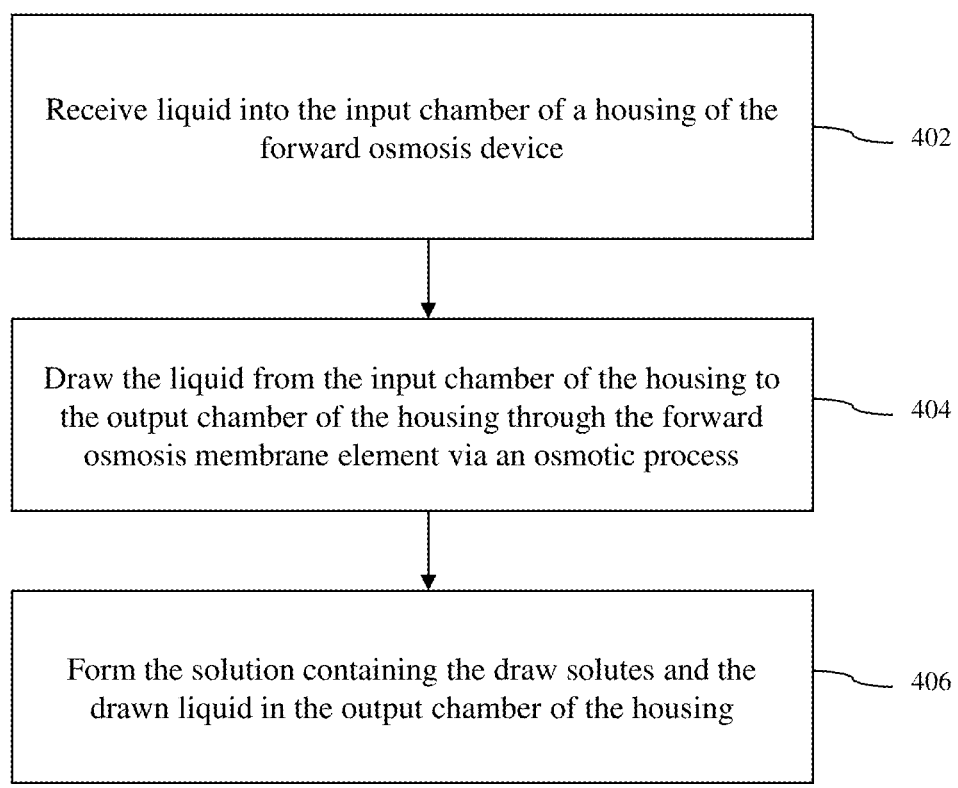
FIG. 4 is a process flow diagram of a method of using a solution produced using a forward osmosis device in accordance with an embodiment of the invention.

A method of using a solution produced using a forward osmosis device that includes a housing having an input chamber and an output chamber separated by a forward osmosis membrane element, the forward osmosis membrane element including a layer of purifying additives on the forward osmosis membrane element, in accordance with an embodiment of the invention is now described with reference to the process flow diagram of FIG. 4. At block 402, liquid is received into the input chamber of a housing of the forward osmosis device. At block 404, the liquid from the input chamber of the housing is drawn to the output chamber of the housing through the forward osmosis membrane element via an osmotic process. The drawing of the liquid through the forward osmosis membrane includes transmitting the liquid through the layer of purifying additives to remove contaminants in the liquid as the liquid is drawn through the forward osmosis membrane element. At block 406, the solution containing the draw solutes and the drawn liquid is formed in the output chamber of the housing.

Figure 5:
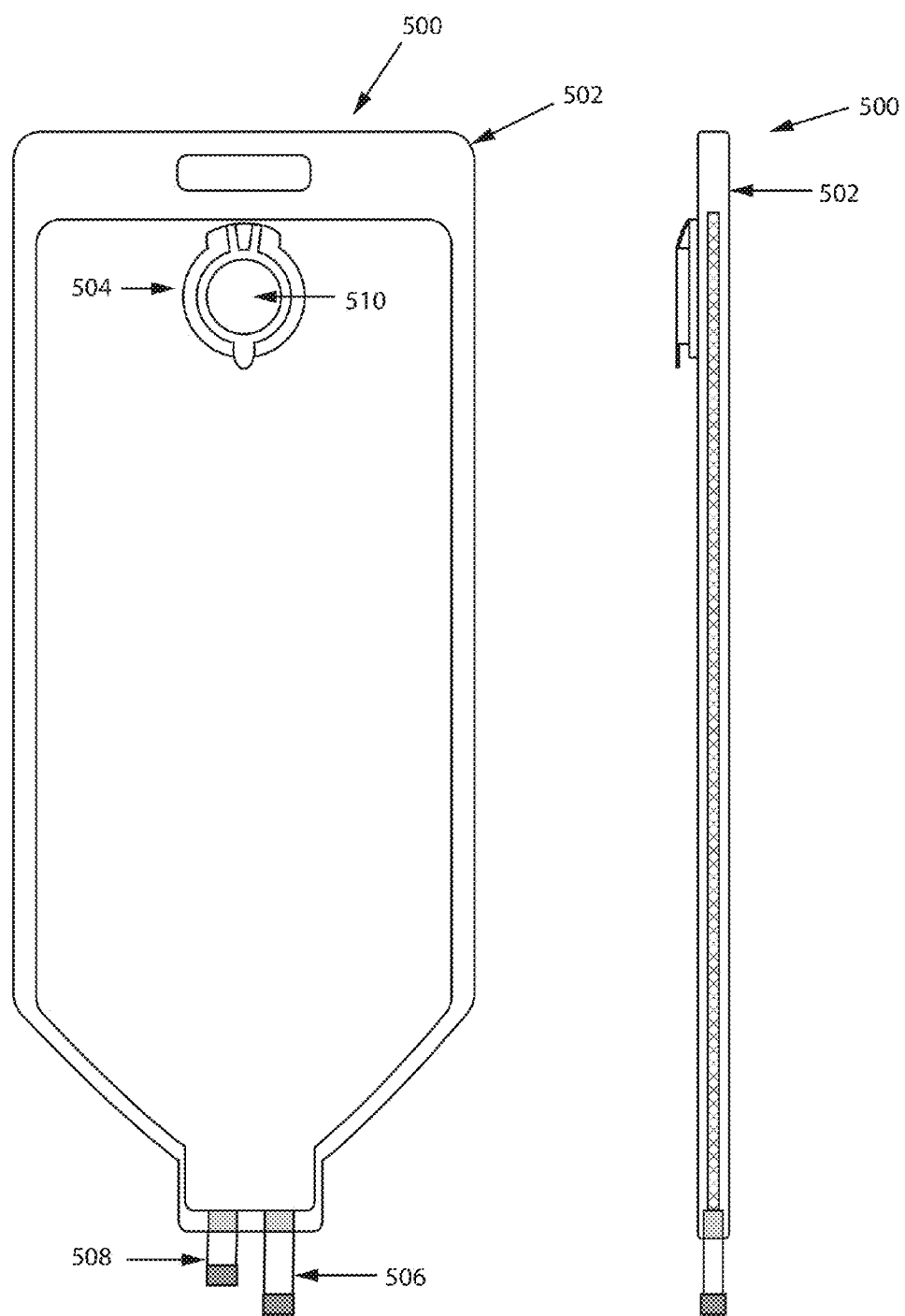
FIG. 5 illustrates the outer packaging of a forward osmosis intravenous (IV) bag in accordance with an embodiment of the invention.
Figure 6:
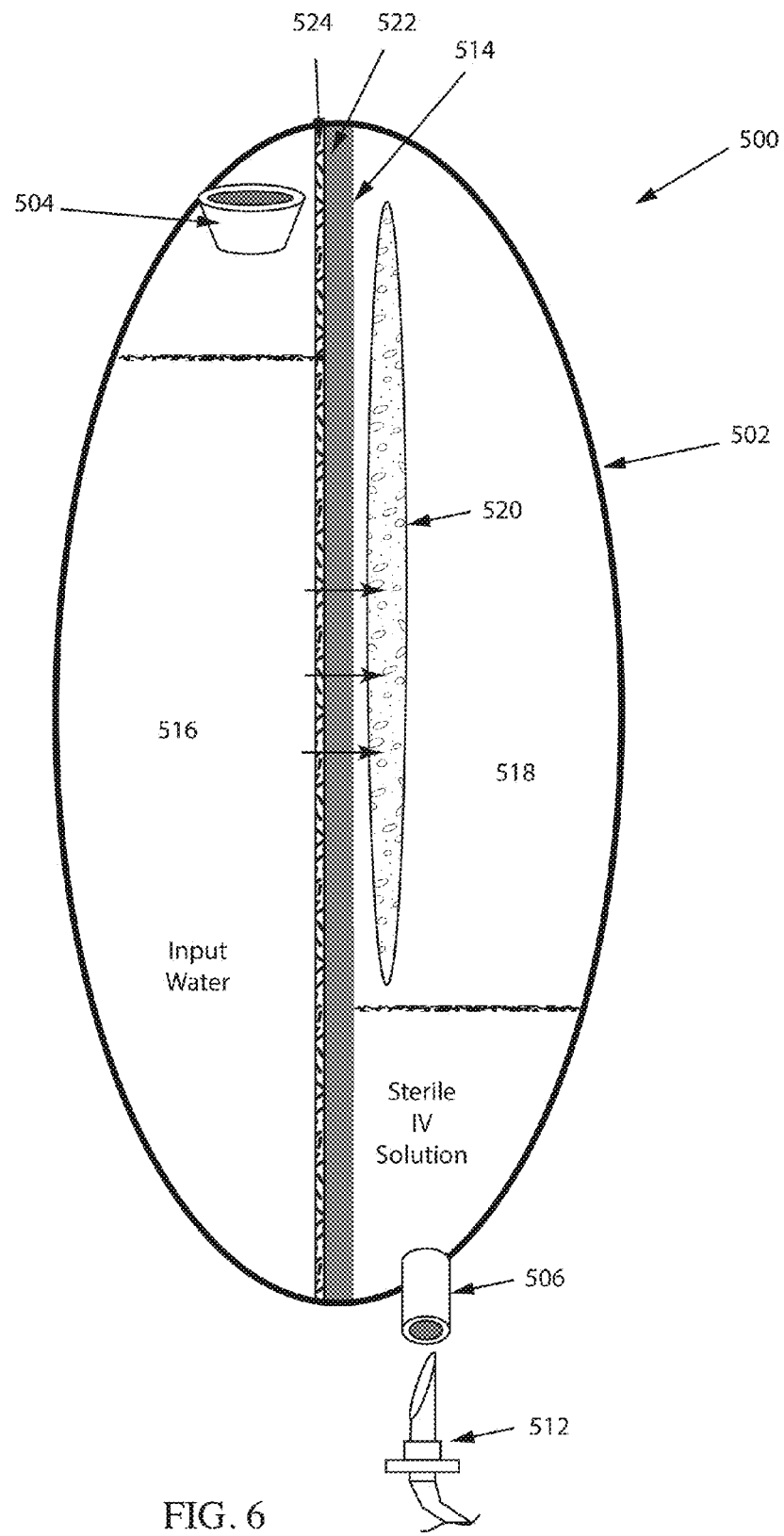
FIG. 6 is a diagram of the forward osmosis IV bag, which shows components of the IV bag, in accordance with an embodiment of the invention.

Turning now to FIGS. 5 and 6, a forward osmosis intravenous (IV) bag 500 in accordance with an embodiment of the invention is shown. FIG. 5 illustrates the outer packaging of the forward osmosis IV bag. In FIG. 5, the front of the forward osmosis IV bag is shown on the left and the side of the forward osmosis IV bag is shown on the right. FIG. 6 illustrates various components of the forward osmosis IV bag. As shown in FIG. 5, the forward osmosis IV bag comprises an IV bag housing 502 with a water intake port 504, an exit IV line port 506 and an optional syringe port 508 (not shown in FIG. 6) for injecting medication into the forward osmosis IV bag using a syringe. The IV bag housing can be made of any flexible and waterproof material. As an example, the IV bag housing can be made of any material currently used to for conventional IV bags, such as a strong plastic film that will resist tear and withstand gamma radiation sterilization. The water intake port 504 is an opening to pour in water, which may include organic and non-organic contaminants. The water intake port 504 is designed to be closed using a closing mechanism 510, such as a plastic cap. The exit IV line port is closed and is designed to be punctured by an IV line 512 (shown in FIG. 6) so that the sterile IV solution in the forward osmosis IV bag, which is produced using any water source, can be delivered to a patient through the IV line. In some embodiments, the exit IV line port can be an exit port commonly found in conventional IV bags. The form factor of the IV bag housing may be the same form factor of conventional IV bags, or may differ from the form factor of conventional IV bags.

As shown in FIG. 6, the forward osmosis IV bag 500 further includes a forward osmosis membrane element 514 in the IV bag housing 502 separating the interior region of the IV bag housing into two chambers, an input chamber 516 connected to the inlet 504 and an output chamber 518 connected to the exit IV line port 506. The input chamber is used to receive input water, which may be dirty or contaminated, that is to be used to produce an IV solution. The output chamber contains draw solutes 520 to draw the input water from the input chamber to the output chamber via an osmotic process. The draw solutes contained in the output chamber may include substance from a "salt" family, such as sodium chloride, potassium chlorides and magnesium chloride, or may include substance from a "sucrose" family, such as sugar and dextrose. These types of draw solutes may be used to produce saline or sucrose solution for IV application. The draw solutes may be in the form of a brine or in the form of solids.

The forward osmosis membrane element 514 includes a forward osmosis membrane 522, which can be any type of forward osmosis membrane. In some embodiments, the forward osmosis membrane element 514 includes one or more layers 524 of purifying additives, such as activated charcoal powder (e.g., coconut shell activated carbon powder) or Hydromethane Sulfinate for ammonia removal, on one or both major surfaces of the forward osmosis membrane to further filter organic and/or nonorganic contaminants in the input water so that the resulting solution is appropriate to be as an IV solution, e.g., satisfies US FDA standards for IV solutions. In an embodiment, the forward osmosis membrane is an asymmetric forward osmosis membrane having a porous non-active layer that has been treated with one or more types of purifying additives, for example, in the manner illustrated in FIG. 2, thereby forming the layer 524 of purifying additives on the non-active layer of the asymmetric forward osmosis membrane. In another embodiment, the layer 524 of purifying additives of the forward osmosis membrane element is a porous substrate containing the purifying additives, which is attached or placed adjacent to the forward osmosis membrane. The porous substrate may be treated with the purifying additives before or after being attached or placed adjacent to the forward osmosis membrane so that the porous substrate contains the purifying additives. The porous substrate may be treated in the same manner illustrated in FIG. 2.

The inlet 504 of the forward osmosis IV bag 500 is connected to the input chamber 516 so that input water can be placed into the input chamber. The input water can be any water readily available at the site where an IV solution is needed for a patient, which may be a remote place. The exit IV line port 506 is connected to the output chamber 518 so that the IV solution produced via an osmotic process using the input water can be administered to the needed patient.

Figure 7:
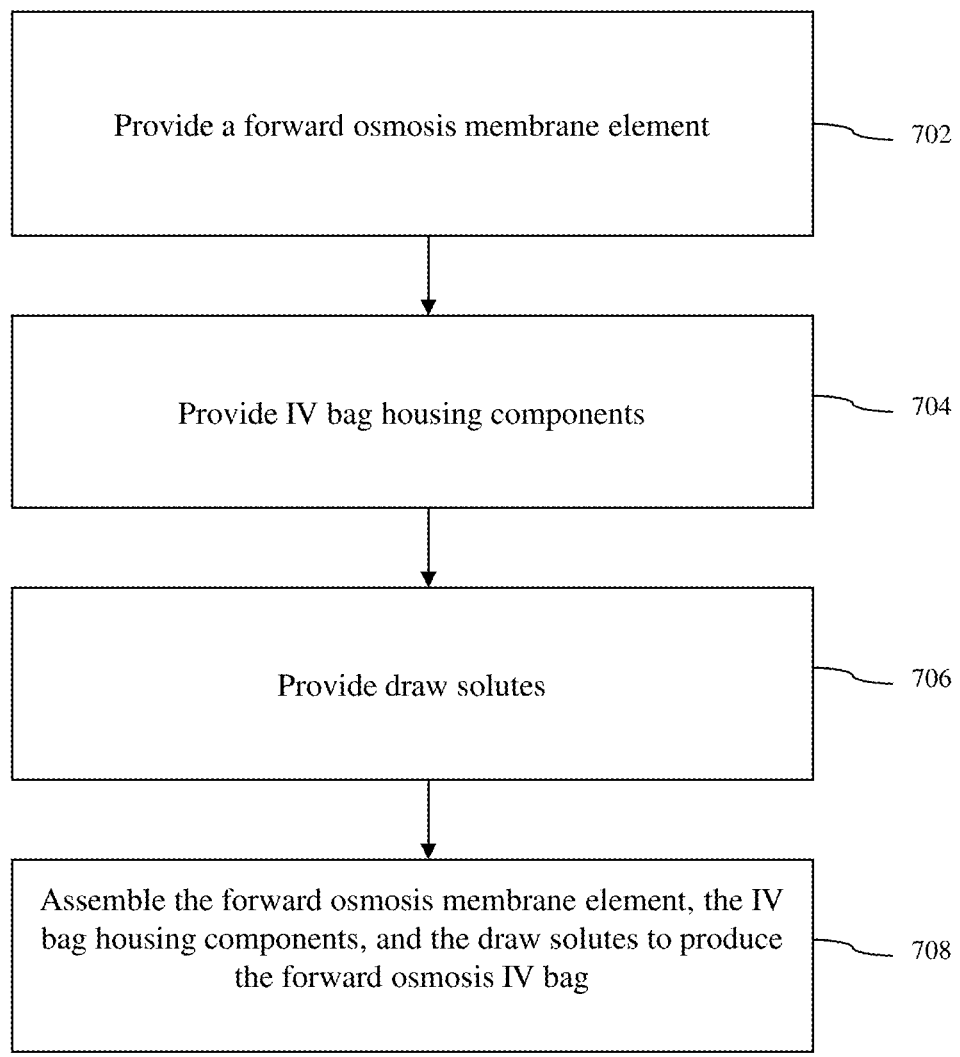
FIG. 7 is a process flow diagram of a method of manufacturing a forward osmosis IV bag in accordance with an embodiment of the invention.

A method of manufacturing a forward osmosis IV bag, such as the forward osmosis IV bag 500, in accordance with an embodiment of the invention is now described with reference to the process flow diagram of FIG. 7. At block 702, a forward osmosis membrane element is provided. At block 704, IV bag housing components are provided. At block 706, draw solutes are provided. At block 708, the forward osmosis membrane element, the IV bag housing components, and the draw solutes are assembled to produce the forward osmosis IV bag that includes an IV bag housing having an input chamber and an output chamber separated by the forward osmosis membrane element. The components of the forward osmosis IV bag are assembled so that the output chamber contains the draw solutes, the IV bag housing includes an inlet configured to receive water into the input chamber that is drawn to the output chamber by the draw solutes through the forward osmosis membrane element to produce a IV solution, and the IV bag housing includes an exit port that is designed to be connected to an IV line.

Figure 8:
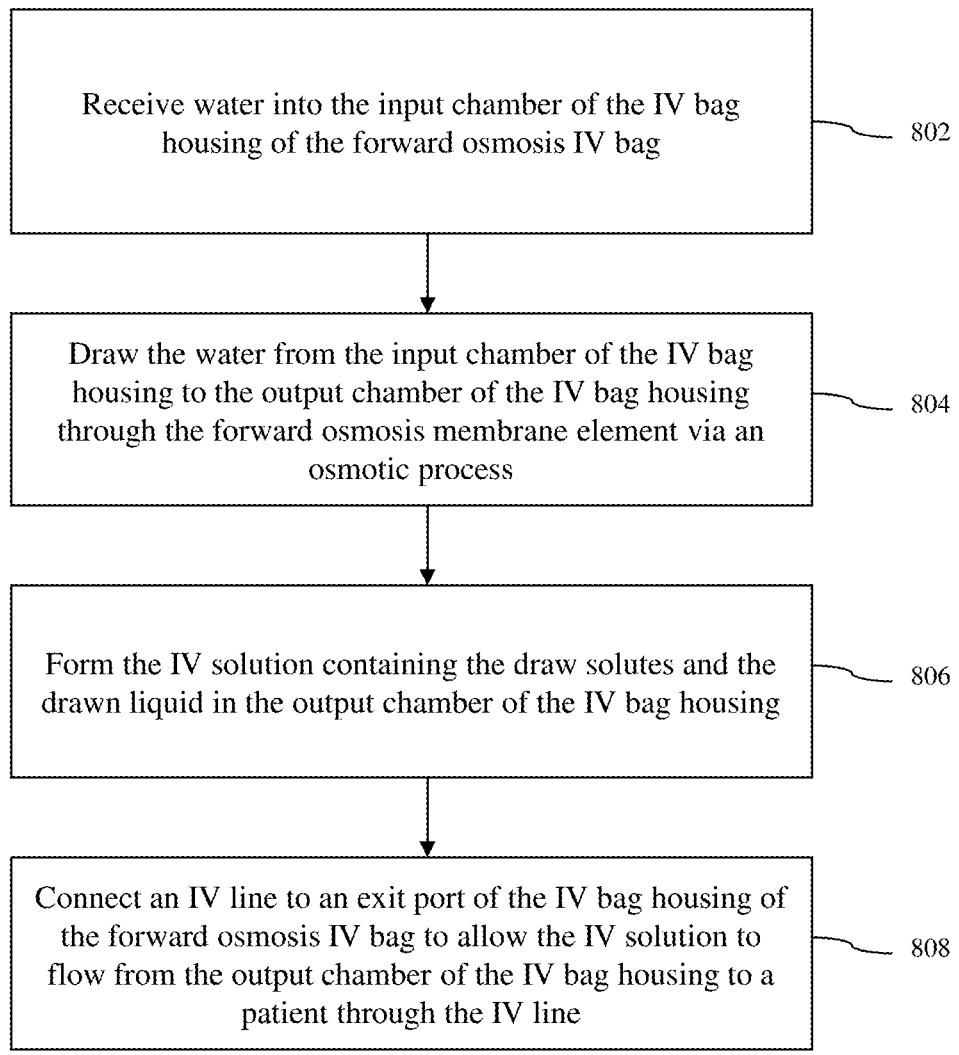
FIG. 8 is a process flow diagram of a method of using an IV solution produced using a forward osmosis IV bag in accordance with an embodiment of the invention.

A method of using an IV solution produced using a forward osmosis IV bag that includes an IV bag housing having an input chamber and an output chamber separated by a forward osmosis membrane element in accordance with an embodiment of the invention is now described with reference to the process flow diagram of FIG. 8. At block 802, water is received into the input chamber of the IV bag housing of the forward osmosis IV bag. At block 804, the water is drawn from the input chamber of the IV bag housing to the output chamber of the IV bag housing through the forward osmosis membrane element via an osmotic process. At block 804, the IV solution containing the draw solutes and the drawn liquid is formed in the output chamber of the IV bag housing. At block 806, an IV line is connected to an exit port of the IV bag housing of the forward osmosis IV bag to allow the IV solution to flow from the output chamber of the IV bag housing to a patient through the IV line.

Figure 9:
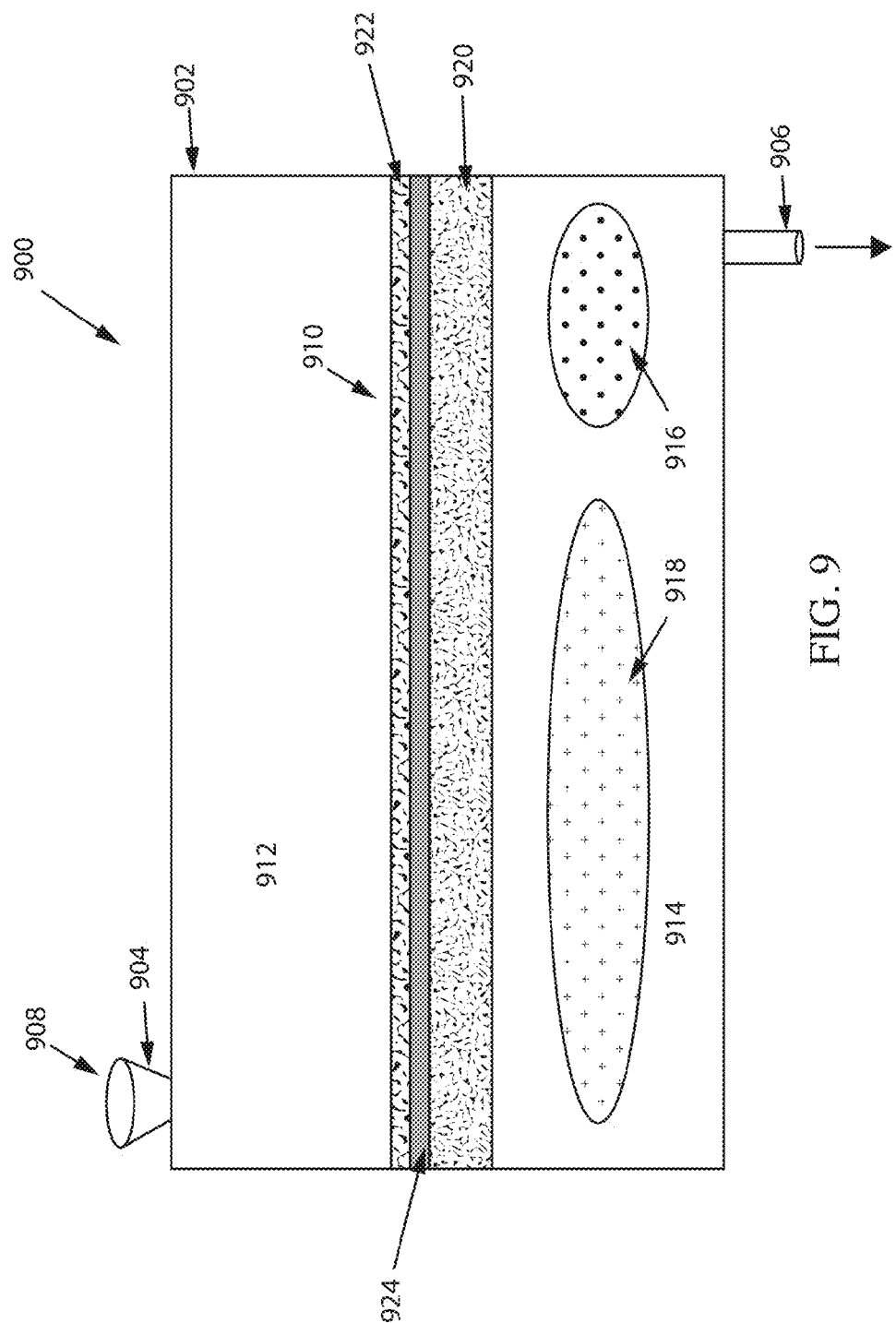
FIG. 9 is a diagram of a drug reconstitution device in accordance with an embodiment of the invention.

Turning now to FIG. 9, a drug reconstitution device 900 in accordance with an embodiment of the invention is shown. As described in detail below, the drug reconstitution device is used to reconstitute intravenously delivered drug that can be mixed with solvent, such as sterile Normal Saline (NS) of 0.9% salinity, to create a usable liquid form of drug at the site of care. Often the powder form of a drug is delivered because the drug can be unstable in a liquid form. Typically, the drug is to be used immediately after reconstitution or within 24 hours or more if it is refrigerated. There are many drugs on the market that can be reconstituted at the site of care, such as Zithromax®, and Azithromyacin, which can be mixed with NS or sterile water to create the final product. In the case of Zithromax, 100 mg of the powder form of drug is mixed with 1 mL of solvent (NS or Water). However, the solvent must be sterile since the final produce will be injected into a patient. For remote areas around the world where drugs are most needed, it may be difficult to ship fully diluted drugs in liquid form since the shelf life of such a product is very short. For example, Vancomycin's shelf life in a powder form is 36 months. However, once the drug has been reconstituted, the drug would only last 24 hours, if kept between 2° C. and 8° C. Therefore, since these drugs are very time sensitive, they are often shipped in a powder form to be reconstituted at the site of care. Unfortunately, areas furthest from the supply chain cannot easily obtain sterile solvents to reconstitute these drugs. The drug reconstitution device resolve this issue of obtaining sterile solvents for drug reconstitution.

Similar to the forward osmosis IV bag 500, the drug reconstitution device 900 comprises a housing 902 with an inlet 904 and an exit port 906. The housing can be made of any waterproof material. As an example, the housing can be made of the same material as an IV bag housing. The inlet is an opening to pour in water, which may include organic and non-organic contaminants. The inlet mat be designed to be closed using a closing mechanism 908, such as a plastic cap. The exit port 906 is closed and is designed to be punctured by an IV line so that a reconstituted drug solution in the drug reconstitution device, which is produced using the input water, can be delivered to a patient through the IV line.

The drug reconstitution device 900 further includes a forward osmosis membrane element 910 in the housing 902 separating the interior region of the housing into two chambers, an input chamber 912 and an output chamber 914. The input chamber is used to receive input water that is to be used to produce a reconstituted drug solution. The output chamber contains draw solutes 916 to draw the input water from the input chamber to the output chamber via an osmotic process. The draw solutes contained in the output chamber may include a substance from a "salt" family, such as sodium chloride, potassium chlorides and magnesium chloride, or may include a substance from a "sucrose" family, such as sugar and dextrose. These types of draw solutes may be used to produce a saline or sucrose solution for reconstitution of drugs. The draw solutes may be in the form of a brine or in the form of solids. The output chamber also contains one or more drugs in power form that is to be reconstituted in liquid form, such as Zithromax®, and Azithromyacin.

The forward osmosis membrane element 910 includes a forward osmosis membrane 920, which can be any type of forward osmosis membrane. In some embodiments, the forward osmosis membrane element 920 includes one or more layers 922 of purifying additives, such as activated charcoal powder (e.g., coconut shell activated carbon powder) or Hydromethane Sulfinate for ammonia removal, on one or both major surfaces of the forward osmosis membrane to further filter organic and/or nonorganic contaminants in the input water so that the resulting solution is appropriate to be as an IV solution, e.g., satisfies US FDA standards for IV solutions. In an embodiment, the forward osmosis membrane is an asymmetric forward osmosis membrane having a porous non-active layer 924 that has been treated with one or more types of purifying additives, for example, in the manner illustrated in FIG. 2, thereby forming the layer 922 of purifying additives on the non-active layer of the asymmetric forward osmosis membrane. In another embodiment, the layer 922 of purifying additives of the forward osmosis membrane element is a porous substrate containing the purifying additives, which is attached or placed adjacent to the forward osmosis membrane. The porous substrate may be treated with the purifying additives before or after being attached or placed adjacent to the forward osmosis membrane so that the porous substrate contains the purifying additives. The porous substrate may be treated in the same manner illustrated in FIG. 2.

The inlet 904 of the drug reconstitution device 900 is connected to the input chamber 912 so that input water can be placed into the input chamber. The input water can be any water readily available at the site to produce a reconstituted drug solution for a patient. The exit port 906 is connected to the output chamber 914 so that the reconstituted drug solution produced via an osmotic process using the input water can be given to the needed patient. As an example, an IV line may be connected to the exit port so that the reconstituted drug solution can be administered to the patient intravenously.

Figure 10:
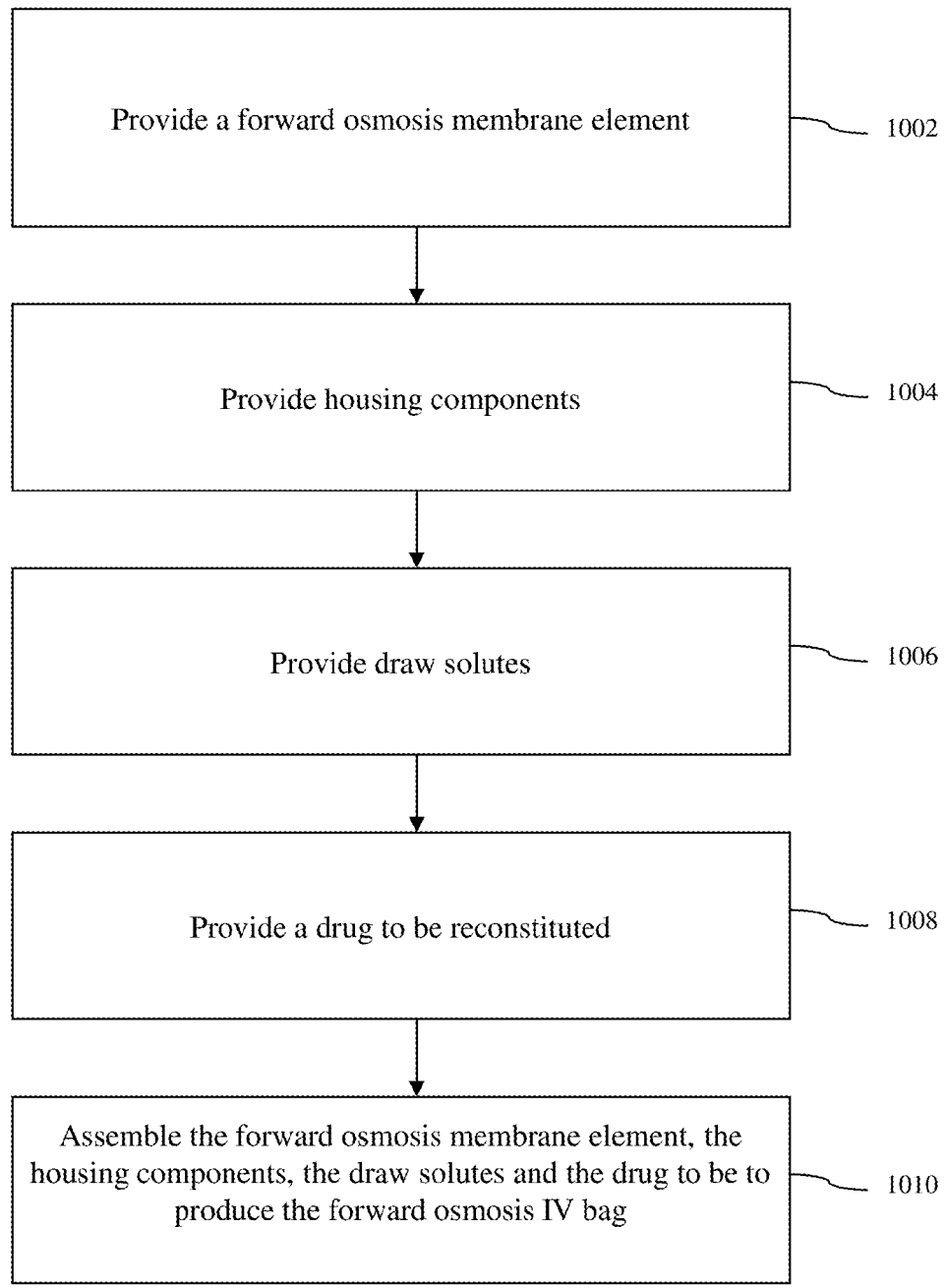
FIG. 10 is a process flow diagram of a method of manufacturing a drug reconstitution device in accordance with an embodiment of the invention.

A method of manufacturing a drug reconstitution device, such as the drug reconstitution device 900, in accordance with an embodiment of the invention is now described with reference to the process flow diagram of FIG. 10. At block 1002, a forward osmosis membrane element is provided. At block 1004, housing components are provided. At block 1006, draw solutes are provided. At block 1008, a drug to be reconstituted is provided. At block 1010, the forward osmosis membrane element, the housing components, and the draw solutes are assembled to produce the drug reconstitution device that includes a housing having an input chamber and an output chamber separated by the forward osmosis membrane element. The components of the drug reconstitution device are assembled so that the output chamber contains the draw solutes and the drug to be reconstituted, and the housing includes an inlet configured to receive water into the input chamber that is drawn to the output chamber by the draw solutes through the forward osmosis membrane element to produce the reconstituted drug solution in the output chamber.

Figure 11:
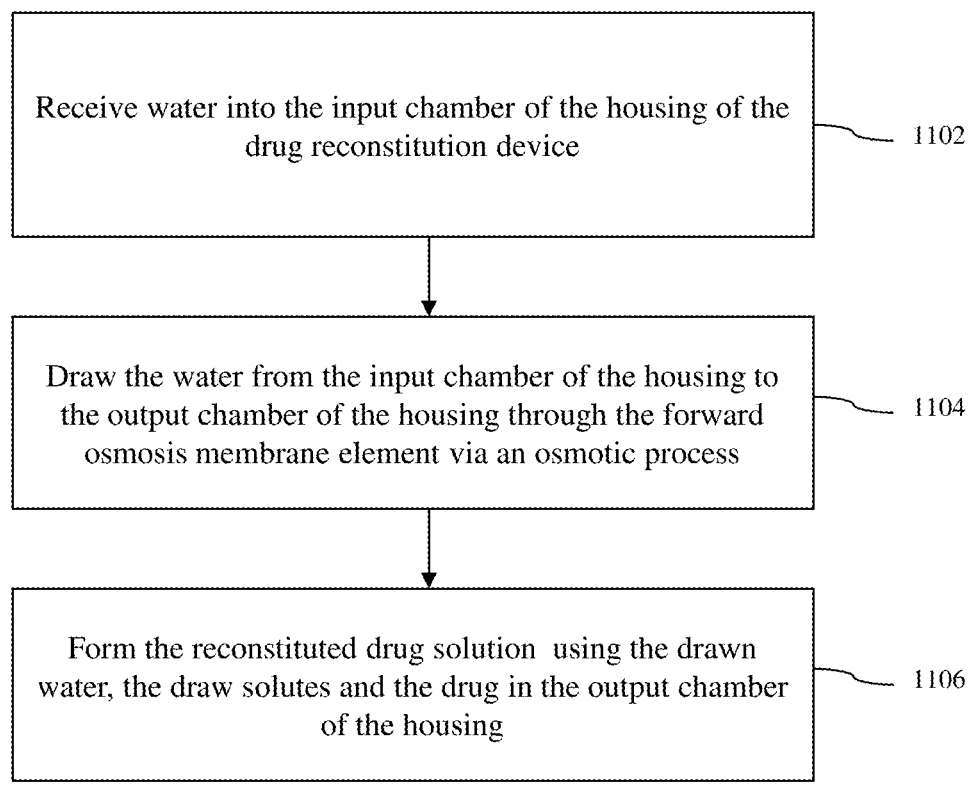
FIG. 11 is a process flow diagram of a method of using a reconstituted drug solution produced using a drug reconstitution device in accordance with an embodiment of the invention.

A method of producing a reconstituted drug solution using a drug reconstitution device that includes a housing having an input chamber and an output chamber separated by a forward osmosis membrane element, the output chamber containing draw solutes and a drug to be reconstituted, in accordance with an embodiment of the invention is now described with reference to the process flow diagram of FIG. 11. At block 1102, water is received into an input chamber of the housing of the drug reconstitution device. At block 1104, the water is drawn from the input chamber of the housing to the output chamber of the housing through the forward osmosis membrane element via an osmotic process. At block 1106, the reconstituted drug solution is produced using the drawn water, the draw solutes and the drug in the output chamber of the housing that can be administered to a patient.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A forward osmosis device comprising:
    a housing having an input chamber and an output chamber, the housing including an inlet connected to the input chamber and an outlet connected to the output chamber;
    draw solutes in the output chamber of the housing; and
    a forward osmosis membrane element positioned within the housing between the input chamber and the output chamber, the forward osmosis membrane element being configured to draw liquid placed in the input chamber through the inlet into the output chamber containing the draw solutes via an osmotic process, the forward osmosis membrane element including a layer of purifying additives on the forward osmosis membrane element to remove contaminants in the liquid as the liquid is drawn through the forward osmosis membrane element,
    wherein the layer of purifying additives includes Hydromethane Sulfinate.

2. The forward osmosis device of claim 1, wherein the forward osmosis membrane element include an asymmetric forward osmosis membrane with a non-active layer and wherein the layer of purifying additives is a coating on the non-active layer of the asymmetric forward osmosis membrane.

3. The forward osmosis device of claim 2, wherein the forward osmosis membrane element includes at least one additional layer of purifying additives that includes activated charcoal powder in base liquid.

4. The forward osmosis device of claim 1, wherein the forward osmosis membrane element include an asymmetric forward osmosis membrane with a porous non-active layer and wherein the layer of purifying additives includes a porous substrate containing the purifying additives attached to the porous non-active layer of the asymmetric forward osmosis membrane.

5. The forward osmosis device of claim 1, wherein the housing is an intravenous bag (IV) housing that includes an exit port that is designed to be connected to an IV line.

6. The forward osmosis device of claim 1, wherein the forward osmosis membrane element, the draw solutes and the purifying additives are configured to produce a solution from the liquid that satisfies guidelines set by US Food and Drug Administration (USFDA) for intravenous use or for cleansing an wound of a patient.

7. A method of manufacturing a forward osmosis device, the method comprising:
    providing a forward osmosis membrane element;
    providing housing components;
    providing draw solutes;
    applying purifying additives onto the forward osmosis membrane element, thereby forming a layer of purifying additives on the osmosis membrane, wherein the layer of purifying additives includes Hydromethane Sulfinate; and
    assembling the forward osmosis membrane element with the layer of purifying additives, the housing components, and the draw solutes to produce the forward osmosis device that includes a housing having an input chamber and an output chamber separated by the forward osmosis membrane, the output chamber containing the draw solutes, the housing including an inlet connected to the input chamber and an outlet connected to the output chamber so that liquid can be placed in the input chamber through the inlet to produce a solution in the output chamber and the solution in the chamber can be accessed through the outlet.

8. The method of claim 7, wherein the forward osmosis membrane element include an asymmetric forward osmosis membrane with a non-active layer and wherein applying the purifying additives includes applying the purifying additives onto the non-active layer to form a coating of purifying additives on the non-active layer of the asymmetric forward osmosis membrane.

9. The method of claim 8, further comprising applying another purifying additives that include activated charcoal powder onto the forward osmosis membrane element or onto the layer of purifying additives to form another layer of purifying additives on the forward osmosis membrane element.

10. The method of claim 7, wherein the forward osmosis membrane element include an asymmetric forward osmosis membrane with a porous non-active layer and wherein applying the purifying additives includes applying the purifying additives onto a porous substrate attached to the porous non-active layer of the asymmetric forward osmosis membrane to form a coating of the purifying additives on the porous substrate.

11. The method of claim 7, wherein assembling includes forming an intravenous bag (IV) housing having an exit port that is designed to be connected to an IV line.

12. The method of claim 7, wherein the forward osmosis membrane element, the draw solutes and the purifying additive mixture are configured to produce the solution that satisfies guidelines set by US Food and Drug Administration (USFDA) for intravenous use or for cleansing a wound of a patient.

13. A method of using a solution produced using a forward osmosis device that includes a housing having an input chamber and an output chamber separated by a forward osmosis membrane element, the forward osmosis membrane element including a layer of purifying additives on the forward osmosis membrane element, the method comprising:
receiving liquid into the input chamber of a housing of the forward osmosis device;
drawing the liquid from the input chamber of the housing to the output chamber of the housing through the forward osmosis membrane element via an osmotic process, including transmitting the liquid through the layer of purifying additives to remove contaminants in the liquid as the liquid is drawn through the forward osmosis membrane element, wherein the layer of purifying additives includes Hydromethane Sulfinate; and
forming the solution containing the draw solutes and the drawn liquid in the output chamber of the housing.

14. The method of claim 13, wherein the forward osmosis membrane element of the forward osmosis device includes an asymmetric forward osmosis membrane with a non-active layer and wherein the layer of purifying additives includes a coating of purifying additives on the non-active layer of the asymmetric forward osmosis membrane.

15. The method of claim 14, wherein the forward osmosis membrane element includes at least one additional layer of purifying additives that includes activated charcoal powder in base liquid.

16. The method of claim 13, wherein the forward osmosis membrane element include an asymmetric forward osmosis membrane with a porous non-active layer and wherein the layer of purifying additives on the forward osmosis membrane element includes a porous substrate containing the purifying additives attached to the porous non-active layer of the asymmetric forward osmosis membrane.

17. The method of claim 13, wherein the housing is an intravenous bag (IV) housing having an exit port, the method further comprising connecting an IV line to the exit port to allow the solution to flow from the output chamber to a patient through the IV line.

18. The method of claim 13, wherein the housing includes an outlet connect to the output chamber, the method further comprising releasing the output liquid from the output chamber via the outlet onto a wound of a patient to cleanse the wound using the solution.

19. A forward osmosis intravenous (IV) bag comprising:
an IV bag housing having an input chamber and an output chamber, the IV bag housing including an inlet connected to the input chamber and an exit port connected to the output chamber, the exit port being designed to be connected to an IV line;
draw solutes in the output chamber of the IV bag housing; and
a forward osmosis membrane element positioned within the IV bag housing between the input chamber and the output chamber, the forward osmosis membrane element being configured to draw water placed in the input chamber into the output chamber containing the draw solutes via an osmotic process to produce an IV solution in the output chamber of the IV bag housing, the output chamber being accessible via the exit port when the exit port is connected to the IV line to allow the IV solution to flow from the output chamber to a patient through the IV line, the forward osmosis membrane element including a layer of purifying additives on the forward osmosis membrane element to remove contaminants in the water as the water is drawn through the forward osmosis membrane element, wherein the layer of purifying additives includes Hydromethane Sulfinate.

20. The forward osmosis IV bag of claim 19, wherein the forward osmosis membrane element include an asymmetric forward osmosis membrane with a non-active layer and wherein the forward osmosis membrane element includes at least one additional layer of purifying additives that includes activated charcoal powder in base liquid.

21. The forward osmosis IV bag of claim 20, wherein the forward osmosis membrane element include an asymmetric forward osmosis membrane with a porous non-active layer and wherein the layer of purifying additives includes a porous substrate containing the purifying additives attached to the porous non-active layer of the asymmetric forward osmosis membrane.

22. A method of manufacturing a forward osmosis intravenous (IV) bag, the method comprising:
providing a forward osmosis membrane element, the forward osmosis membrane element including a layer of purifying additives on the forward osmosis membrane element, wherein the layer of purifying additives includes Hydromethane Sulfinate;
providing IV bag housing components;
providing draw solutes; and
assembling the forward osmosis membrane element, the IV bag housing components, and the draw solutes to produce the forward osmosis IV bag that includes an IV bag housing having an input chamber and an output chamber separated by the forward osmosis membrane element, the output chamber containing the draw solutes, the IV bag housing including an inlet configured to receive water into the input chamber that is drawn to the output chamber by the draw solutes through the forward osmosis membrane element to produce a IV solution, the IV bag housing further including an exit port that is designed to be connected to an IV line.

23. The method of claim 22, wherein the forward osmosis membrane element include an asymmetric forward osmosis membrane with a porous non-active layer and wherein the layer of purifying additives includes a porous substrate containing the purifying additives attached to the porous non-active layer of the asymmetric forward osmosis membrane.

24. A method of using an intravenous (IV) solution produced using a forward osmosis IV bag that includes an IV bag housing having an input chamber and an output chamber separated by a forward osmosis membrane element, the method comprising:
receiving water into the input chamber of the IV bag housing of the forward osmosis IV bag;
drawing the water from the input chamber of the IV bag housing to the output chamber of the IV bag housing through the forward osmosis membrane element via an osmotic process, the forward osmosis membrane element including a layer of purifying additives on the forward osmosis membrane element to remove contaminants in the water as the water is drawn through the forward osmosis membrane element, wherein the layer of purifying additives includes Hydromethane Sulfinate;

forming the IV solution containing the draw solutes and the drawn liquid in the output chamber of the IV bag housing; and connecting an IV line to an exit port of the IV bag housing of the forward osmosis IV bag to allow the IV solution to flow from the output chamber of the IV bag housing to a patient through the IV line.

25. The method of claim 24, wherein the forward osmosis membrane element include an asymmetric forward osmosis membrane with a non-active porous layer and wherein the layer of purifying additives includes a porous substrate containing the purifying additives attached to the porous non-active layer of the asymmetric forward osmosis membrane.

\* \* \* \* \*